United States Patent
Mihaylov

(10) Patent No.: US 7,670,619 B2
(45) Date of Patent: Mar. 2, 2010

(54) CONTROLLED-RELEASE FORMULATIONS CONTAINING TRYPTOPHAN OR ITS METABOLITES

(75) Inventor: Bojidar Mihaylov, Milan (IT)

(73) Assignee: Ambros Pharma S.r.l., Milan (IT)

( * ) Notice: Subject to any disclaimer, the term of this patent is extended or adjusted under 35 U.S.C. 154(b) by 885 days.

(21) Appl. No.: 11/201,070

(22) Filed: Aug. 9, 2005

(65) Prior Publication Data

US 2006/0045913 A1    Mar. 2, 2006

(30) Foreign Application Priority Data

Sep. 1, 2004    (IT)    .......................... MI2004A1689

(51) Int. Cl.
*A61K 9/20* (2006.01)
*A61K 31/05* (2006.01)

(52) U.S. Cl. ...................................... 424/464; 514/415

(58) Field of Classification Search ................. 514/415; 424/464

See application file for complete search history.

(56) References Cited

U.S. PATENT DOCUMENTS

2002/0147155 A1    10/2002    Foster et al.

FOREIGN PATENT DOCUMENTS

| EP | 1077065 | A | 2/2001 |
|----|---------|---|--------|
| GB | 1378296 | A | 12/1974 |

OTHER PUBLICATIONS

European Search Report.

*Primary Examiner*—Sreeni Padmanabhan
*Assistant Examiner*—Renee Claytor
(74) *Attorney, Agent, or Firm*—Hedman & Costigan, P.C.; James V. Costigan

(57) ABSTRACT

New controlled-release formulations containing tryptophan and/or its metabolites are described, as well as the process to obtain them in tablet forms suitable for oral administration in the treatment of pathologies or conditions related to serotonin deficiency in the Nervous System. The formulations are comprised in double-layer tablets, one layer containing 5-hyrohytryptophan released rapidly (phase "fast"), the other layer containing tryptophan or 5-hydroxytryptophan, progressively released ("retarded"). The finished product is characterized by optimal differential release profile under physiological conditions. In all cases the release kinetics obtained is accurately time- and concentration-controlled, therefore avoiding fortuitous release of the active ingredients, and in clinical setting is free of undesirable side effects.

14 Claims, 1 Drawing Sheet

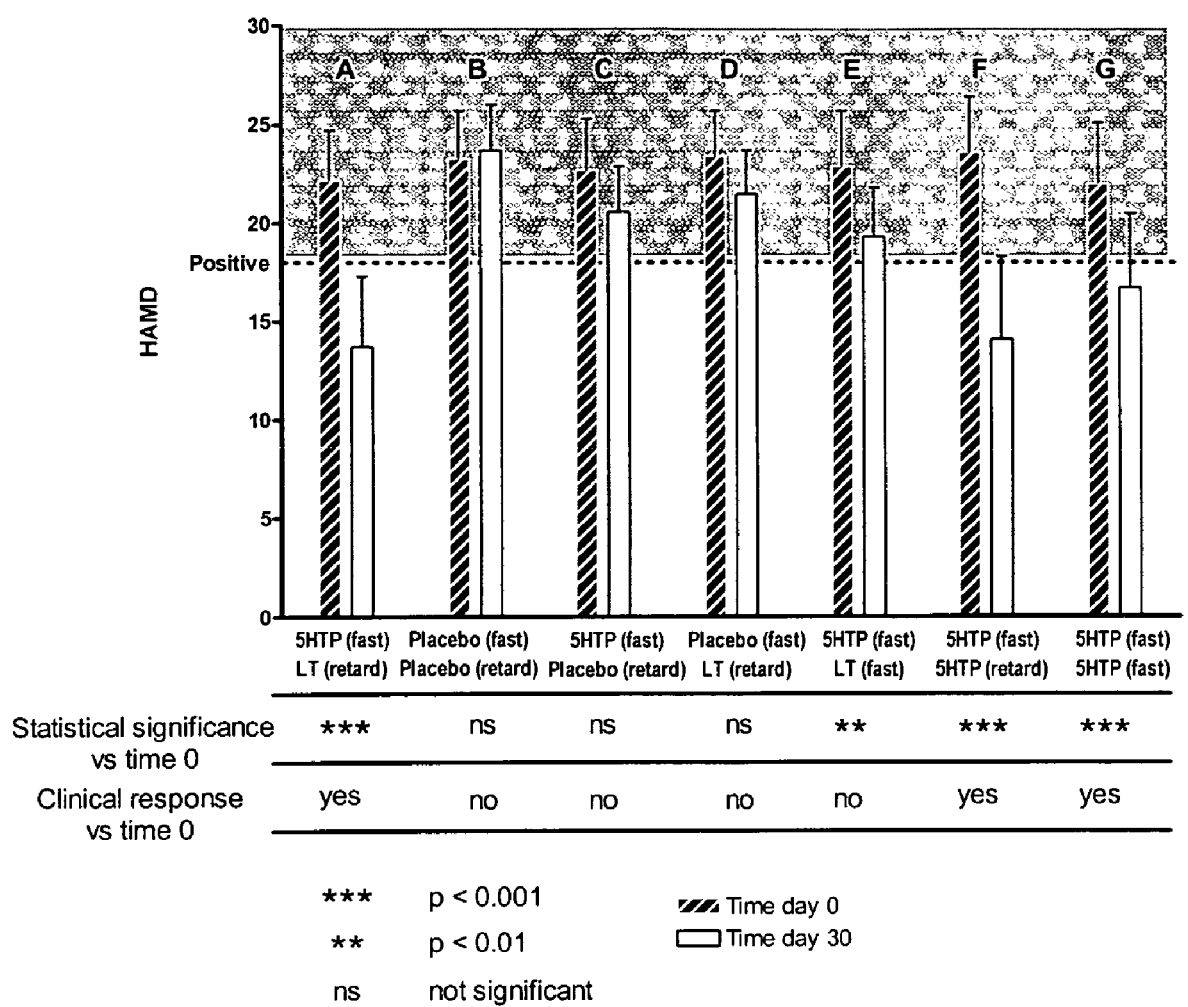
Figure 1: Mean HAMD score ± S.D. (treatments vs time) in the study groups

CONTROLLED-RELEASE FORMULATIONS CONTAINING TRYPTOPHAN OR ITS METABOLITES

FIELD OF INVENTION

The present invention relates the use of tryptophan (Trp) and/or its metabolites, in particular 5-hydroxytryptophan (5-HTP), in the treatment of serotonin deficiency in the Central Nervous System (CNS).

BACKGROUND OF THE INVENTION

5-HTP and Trp, which are precursors of serotonin, represent a significant approach in the treatment of conditions that involve serotonin synthesis and release in the CNS. The main interest in the use of Trp and its metabolites derives from the fact that they represent a natural alternatives to traditional antidepressants, such as for example, the selective serotonin reuptake inhibitors (SSRI), and minor long-term adverse effects are expected when using 5-HTP and Trp. Among the pathologies or conditions associated with serotonin deficiency in the Nervous System are the mood disturbances, the depression, the fibromylagia syndrome, the serotonin-dependent headache, the overweight and the obesity. The use of a direct supplementation with serotonin is not applicable because serotonin does not cross the blood-brain barrier (BBB). Trp is transported across the BBB by means of a carrier mechanism, while 5-HTP crosses easily the BBB.

The synthesis of serotonin, both centrally and peripherally, starts with hydroxylation of Trp to 5-HTP by means of 5-tryptophan-hydorxylase, the rate-limiting enzyme in the serotonin synthesis, as other compounds, like proteins, niacin or kynurenines are also synthesized from Trp. 5-HTP is subsequently converted to serotonin by an aromatic amino acid decarboxylase (MAD) that depends on pyridoxine as coenzyme. It has been well documented (J H Juhl, "*Fibromylagia and the Serotonin Pathway*", Altern Med Rev 1998; 3 5 L. 365-375) that the amount of Trp transformed in serotonin is between 2 to 10% of the total Trp present. Excess Trp induces the enzyme pyrrolase and thus deviates Trp metabolism in the direction of the kynurenine pathway leading to the synthesis of niacin, kynurenines and picolinic acid (I. P. Lapin, *Epilepsia*, 22:257 1981).

Because of those peculiarities in the serotonin synthesis, it is essential that Trp should be administered in quantities that would prevent overloading the serotonin-conversion pathway, thus avoiding that the corresponding substrates (in the case Trp and 5-HTP) are utilized in an inefficient manner for synthesis of serotonin, therefore leading to undesirable metabolic outcome. Maintaining bioavailable Trp levels for longer periods of time would allow for a better therapeutic efficacy with lower dosages, overcoming the appearance of potential side effects caused by acute administration of elevated quantities of Trp or 5-HTP. Considering that the rate-limiting step in the serotonin synthesis is the conversion of Trp to 5-HTP, the specific metabolic requirements would be those that hamper a massive release of Trp in the gastrointestinal tract, as it is known that high concentrations of 5-HTP provoke side-effects such as nausea and/or epigastric burning.

On the other hand, in order to obtain a rapid and efficient therapeutic response it is essential to supply promptly an adequate quantity a serotonin precursor, without overloading the enzymatic conversion steps. The currently available formulations do not take into consideration the peculiarities of the serotonin synthesis and actually no formulations containing 5-HTP and Trp that satisfy the metabolic requirements of the organism are available.

SUMMARY OF THE INVENTION

It has been found now that tablets containing one or two active ingredients (Trp and/or 5-HTP), if manufactured under appropriate conditions, obtain not only the properties of releasing immediately one part, containing for example 5-HTP, but also to modulate in time, in a highly efficient manner, the release of Trp or its metabolites, thus gaining therapeutic benefits.

The tablets according to the present invention, having the abovementioned properties were obtained by means of manufacturing double-layer tablets, one layer containing for example 5-HTP released rapidly (phase "fast"), the other layer containing for example Trp, released progressively (phase "retarded"). The finished product is characterized by specific composition and optimal differential release profile under physiological conditions. The phase "fast" releases rapidly 5-HTP and the phase "retard" releases progressively Trp or 5-HTP. In all cases the release kinetics obtained is time- and concentration-controlled, therefore avoiding fortuitous release of the active ingredients, and in controlled clinical trial conditions is free of undesirable side effects. As used herein the term "fast" release means that at least 95% of the active ingredient is released in less than 30 minutes, and preferably less than 5 minutes after testing in a USP Type 2 apparatus at 37C at a paddle speed of 100 rpm with an simulated gastric fluid at pH 2.0 and the term "retarded" release means that not more than 25% is released in 2 hours and not less than 90% of the active ingredient is released in 14, preferably not less than 7 hours after testing in a USP Type 2 apparatus at 37C at a paddle speed of 100 rpm in simulated intestinal fluid at pH 7.5.

BRIEF DESCRIPTION OF THE SEVERAL VIEWS OF THE DRAWINGS

FIG. 1 shows the mean±S.D. of the HAMD score (treatment vs time) in the treatment groups.

The graph indicates the statistical differences and the objective clinical response in the treatment groups. The 21-symptoms *Hamilton Depression Scale* (HAMD) was applied to measure the treatment outcome. The HAMD questionnaire was completed two times: at day 0 (before treatment start) and after 30 days of treatment (day 30). The statistical evaluation of day 30 vs day 0 is reported. Reduction of the HAMD score under the value of 18 (dotted line) indicates positive clinical response to the treatment.

DETAILED DESCRIPTION OF THE INVENTION

The first object of this invention is the manufacturing process of tablets for a differentiated and controlled release of Trp and/or 5-HTP, characterized by the following steps:
  a. separate preparation of the two blends for the "fast" and "retard" layers.
  b. addition of magnesium stearate as last component to each blend.
  c. compression with an appropriate tableting device that ensures the separation, the integrity and release characteristics of each layer.

The procedures of mixing and compressing to obtain the tablets in steps a, b and c are those commonly known and used for production purposes.

The double-layer tablets obtained in this manner and better described hereinafter acquire not only the necessary properties of releasing immediately one active ingredient from one layer (for example 5-HTP), but also those to modulate in time the release of other active ingredients (Trp or 5-HTP) from the other layer.

Both active ingredients (Trp and/or 5-HTP) of the tablets according to the invention can be of synthetic or natural origin (vegetable or animal extracts), as for example extract of *Griffonia simplicifolia* (containing 5-HTP) or all other kinds of extracts of various origin containing Trp or 5-HTP. The tablets may also contain other active ingredients, as pharmaceuticals, or other extracts of vegetable or animal origin, or vitamins, minerals et c., together with excipients commonly used in the preparation of pharmaceuticals or food supplements.

The tablets themselves therefore represent a further object of the invention. They may have a diameter, generally comprised between 0.5 to 1.2 cm, a shape suitable for oral administration and may contain all necessary excipients, colorants and additives, if necessary. The active principles contained in each tablet correspond to those required for a dosage unit.

The tablets obtained with the process according to the invention, present optimal dissolution characteristics in physiological environment and release the active ingredients with a predetermined controlled pattern. In particular, it has been found that this two-phase controlled-release pattern clearly shows a synergic therapeutic effect of the active ingredients, significantly higher than that obtained by the sum of the therapeutic effects of the single active ingredients or the simple administration of the active ingredients together. Additionally, no side-effects were registered, contrary to what obtained with the same dosages of some of the active ingredients administered in a single phase ("fast").

Therefore, a further object of the present invention is the use of the described tablets in the treatment of pathologies or conditions related to the synthesis and the release of serotonin in the Nervous System such as mood disturbances, depression, fibromyalgia, headache, overweight and obesity.

The compositions associated with the present invention may be used for the preparation of food supplements, or foods, and may also contain vitamins, minerals, amino acids, fatty acids, antioxidants, or other nutrients, that is, preparations which in a complex dietary management programme may integrate the diet in individuals presenting intra- and/or extra-cellular deficiencies in the above components and therefore with altered metabolic processes.

The present invention is therefore illustrated by the following non-limiting examples:

EXAMPLE 1

| Name | mg/cpr | % |
|---|---|---|
| Components in the "fast" layer | | |
| 5-Hydroxytryptophan | 50.50 | 13.29 |
| Dicalcium phosphate | 230.00 | 60.53 |
| Microcrystalline cellulose | 93.06 | 24.50 |
| Silicon dioxide | 3.00 | 0.79 |
| Vegetable magnesium stearate | 3.20 | 0.84 |
| Colorant: E132 | 0.23 | 0.06 |
| TOTAL | 380.00 | |
| Components in the "retard" layer | | |
| Tryptophan | 250.00 | 64.10 |
| Hydroxypropyl-methyl cellulose* | 51.00 | 13.08 |
| Dicalcium phosphate | 62.00 | 15.90 |
| Silicon dioxide | 4.00 | 1.03 |
| Vegetable magnesium stearate | 7.00 | 1.79 |
| Talc | 4.00 | 1.03 |
| Vitamin PP | 10.80 | 2.77 |
| Vitamin B6 | 1.20 | 0.31 |
| TOTAL | 380.00 | |

The components reported hereinabove are mixed pressed to form a double layer tablet following the procedures as described below.
*Methocel E4MP having a nominal viscosity of 4000 mPa s for a 2% aqueous solution.

Preparation of the "Fast" Layer:
1. mix the colorant in a portion of microcrystalline cellulose (previously calibrated on a 0.7 mm mesh);
2. mix in a bi-cone mixer all the components (previously calibrated with on a 0.7 mm mesh) for about 10 minutes, with the exception of magnesium stearate;
3. add magnesium stearate at the end of the previous operation and continue mixing for additional 5 minutes.

Preparation of the "Retarded" Layer:
1. add all the components (previously calibrated on a 0.7 mm mesh) in a bi-cone mixer and mix for about 10 minutes with the exception of magnesium stearate;
2. at the end of the previous operation add magnesium stearate and mix for additional 5 minutes.

The hydroxypropyl methylcellulose (HPMC) will have a viscosity which is sufficiently high that it will provide a controlled release of the tryptophan. Generally the HPMC will have a viscosity of 2500 to 100,000 mPa's as measured in a 2% w/v aqueous solution. The preferred HPMC is Methocel E4MP which has a viscosity of 3500-5600, preferably about 4000 mPa's as measured in a 2% w/v aqueous solution.

Compression:
The prepared mixtures are loaded separately through the respective doorways in a tabletting machine (e.g. MANESTY LP) and tablet compression is carried on.

Reference Parameters:
1. hardness: about 5-6 kP (as sum of the double-layer hardness)
2. thickness: about 5.5 mm
3. weight: about 800 mg
4. dissolution in physiological environment:
   "fast" layer: in less than 5 minutes;
   "retard" layer: between 5 and 7 hours

EXAMPLE II

Clinical Evaluation of the Product

A clinical evaluation of the therapeutic effectiveness of the tablets subject of the present invention, prepared as in the Example 1, was performed by using the 21 point *Hamilton Depression Scale* test (HAMD) in subjects suffering of mild depression (mean±S.D. HAMD score 22.87±0.61): 20 subjects per group, 7 groups, 50% males, 50% females, aged between 35 to 75 years. The HAMD score test is well known in diagnostic evaluation of depressive states (Williams, J. B. W., "A Structured Interview Guide for the Hamilton Depression Rating Scale," *Archives of General Psychiatry*, American Medical Association, August 1988, Vol. 45, Num. 8, pp. 742-747). The HAMD questionnaires were completed at day 0 (before the treatment start) and at the end of 30 days of treatment (two tablets per day, oral administration: one in the morning and one at midday). Side effects were registered for each patient as "no side effects", "mild side effects" or "serious side effects". In the case of serious side effects the respective treatment was suspended (physician's decision) as was the case with the test group G, where only 10 subjects completed the study.

The study was designed as a double-blind, controlled with placebo and the respective controls with the single active components. The active ingredients were completely released in a predetermined manner (dissolution test) as follows: phase "fast" within 5 minutes; phase "retard" gradually between first and seventh hour. The tablets were prepared as in Example 1, with the contents and mode of release of the active ingredients as follows:

Group A: 50 mg 5-HTP fast+250 mg Trp retard;

Group B: placebo fast+placebo retard;

Group C: 50 mg 5-HTP fast+placebo retard;

Group D: placebo fast+250 mg Trp retard;

Group E: 50 mg 5-HTP fast+250 mg Trp fast

Group F 50 mg 5-HTP fast+100 mg 5-HTP retard;

Group G: 50 mg 5-HTP fast+100 mg 5-HTP fast (=150 mg 5-HTP fast).

Generally the fast layer will contain 5-hydroxytryptophan and the 5-hydroxytryptophan contents being comprised between 1 and 40% in weight of the layer. The retarded layer may comprise 5-hydroxytryptophan contents in the amount of between 6 and 25% in weight The dose of 50 mg for 5t-HTP and 250 mg for Trp may be varied as necessary to obtain a desired effect. Generally from 25-100 mg of 5HTP and from 100-300 mg of TRP may be utilized.

The subjects were treated for 30 consecutive days, orally with two tablets daily: one in the morning, one at midday. All tablets appeared the same: double-layer tablets, the layers being colored in blue and white, respectively.

The statistical evaluation was performed by using two-way ANOVA combined for the identification of differences between time (time 0 vs time 30) and between groups at day 0 and 30. The clinical response was considered successful if at day 30 the HAMD score was below 18 points.

Table 1 shows the evaluation of the HAMD for all groups at day 0 and day 30, respectively, as well as the corresponding difference (Δ vs day 0=therapeutic efficacy [TE]). The number of the subjects that completed the trial is indicated in column N.

At day 0 all the groups showed a very similar mean HAMD score level comprised between 22.2 and 23.4.

TABLE 1

HAMD score evaluation in the treatment groups.

| | | Day 0 | | | Day 30 | | | Δ vs day |
|---|---|---|---|---|---|---|---|---|
| | | Mean | SD | N | Mean | SD | N | 0 (TE) |
| A | 5HTP (fast) Trp (retard) | 22.2 | 2.5 | 20 | 13.7 | 3.6 | 20 | −8.45 |
| B | Placebo (fast) Placebo (retard) | 23.3 | 2.4 | 20 | 23.7 | 2.3 | 20 | 0.40 |

TABLE 1-continued

HAMD score evaluation in the treatment groups.

| | | Day 0 | | | Day 30 | | | Δ vs day |
|---|---|---|---|---|---|---|---|---|
| | | Mean | SD | N | Mean | SD | N | 0 (TE) |
| C | 5-HTP (fast) Placebo (retard) | 22.7 | 2.6 | 20 | 20.6 | 2.3 | 20 | −2.10 |
| D | Placebo (fast) Trp (retard) | 23.4 | 2.3 | 20 | 21.5 | 2.2 | 20 | −1.95 |
| E | 5HTP (fast) Trp (fast) | 22.9 | 2.8 | 20 | 19.3 | 2.5 | 20 | −3.60 |
| F | 5HTP (fast) 5HTP (retard) | 23.6 | 2.8 | 20 | 14.1 | 4.2 | 20 | −9.55 |
| G | 5HTP (fast) 5HTP (fast) | 22.0 | 3.1 | 10 | 16.7 | 3.8 | 10 | −5.33 |

FIG. 1 reports in graphic form the data contained in table 1.

From the results reported is clear that treatment with the combination of the active ingredients 50 mg 5-HTP fast+250 mg Trp retard (Group A), results in a significant clinical improvement, contrary to what observed in group B (complete placebo control) or in the patients treated with the separate active ingredients (groups C and D). The positive clinical outcome (score below 18 points) is clearly sustained by the net statistical significance ($p<0.001$).

Among those groups, only patients in group A arrived at a score below 18 points. Group B (complete placebo control) shows absence of clinical response whatsoever. Groups C and D (partial placebo) show a slight improvement only, always above the critical level of 18 HAMD score, meaning lack of therapeutic response.

The results described in Table 2 focus on the therapeutic effects (TE) and the side effects induced by the treatment comparing the group A vs group C and group D. The sum of TE in the groups C and D is also reported.

TABLE 2

Therapeutic and side effects in treatment groups A, C and D

| | | Δ vs day 0 (TE) | Statistical significance Sum of TE | Side effects |
|---|---|---|---|---|
| A | 5HTP (fast) Trp (retard) | −8.45 | $p < 0.001$ | 0/20 |
| C | 5-HTP (fast) Placebo (retard) | −2.1 | −4.05 | 0/20 |
| D | Placebo (fast) Trp (retard) | −1.95 | | 0/20 |

From the data in Table 2 it is evident that the concomitant administration of the active ingredients 5-HTP as "fast" and Trp as "retard", produce a result undoubtedly superior to what obtained with the sum of the effects administered as single active ingredients under the same release conditions (groups C and D, respectively). The therapeutic effect obtained in group A is much superior compared to the additive therapeutic effect obtained with the single compounds and the difference is highly significant ($p<0.001$), showing a clear synergic effect of the active ingredients in the formulation.

TABLE 3

Therapeutic and side effects in treatment groups A and E

| | | Δ vs day 0 (TE) | Statistical significance | Side effects |
|---|---|---|---|---|
| A | 5HTP (fast) Trp (retard) | −8.45 | P < 0.05 | 0/20 |
| E | 5-HTP (fast) Trp (fast) | −3.60 | | 0/20 |

The data in Table 3 draw the attention on the comparison between the therapeutic and side effects produced in the treatment groups A and E. The difference between the two treatment groups is only in the timing of Trp release: "retard" in A and "fast" in E. There is a highly significant difference between the clinical response (−8.45 [A] vs −3.60 [E]). Only the patients of group A arrived under 18 HAMD score points. This comparison shows clearly an unexpected synergic activity between the two active ingredients (5-HTP and Trp) when administered according to the present invention, that is, low 5-HTP doses rapidly released ("fast"), together with moderate dosages of Trp released in protracted manner ("retard"). The results were statistically significant with a value of p<0.05.

The results from treatment groups F and G (Table 4) demonstrate another interesting aspect of the present invention. The results obtained in group G demonstrate that the synergic effect observed in group A is not limited to the formulation as illustrated in Example 1, but also applies to other combinations of active ingredients. It can be noted that the administration of alone 5-HTP, concomitantly in the form of "fast" and "retard", shows a therapeutic effect similar to that obtained in treatment group A (see FIG. 1 and Table 1). From statistical viewpoint the difference between A and F was not significant: −8.45 (A) vs −9.55 (F), p>0.05.

TABLE 4

Therapeutic and side effects in treatment groups F and G

| | | Δ vs day 0 (TE) | Statistical significance | Side effects |
|---|---|---|---|---|
| F | 5HTP (fast) 5HTP (retard) | −9.55 | P < 0.01 | 1/20 (mild) |
| G | 5-HTP (fast) 5-HTP (fast) | −5.33 | | 6/10 (mild) 4/10 (serious) |

The results obtained in treatment group G reflect what has been known regarding standard administration of 5-HTP (as "fast" release). There is a modest clinical outcome (slightly below 18 HAMD score points), but the level of the observed side effects is elevated. As a consequence 10 out of 20 subjects completed the study and all showed side effects (nausea, epigastric burning) ranging from mild to serious. Modifying the release pattern according to the present invention a significant clinical result was obtained (Δ vs day 0=−9.55) with a single case of registered side effects (mild) out of 20 patients, that all completed the study, contrary to what observed in group G.

It can be concluded that the controlled-release mode of administration of the active ingredients according to the present invention is crucial to obtain significant clinical response free of side effects.

The invention claimed is:

1. A bi-layer tablet for the treatment of conditions associated with serotonin deficiencies in the nervous system having a fast layer and a retard layer, said fast layer being a layer which possesses a rapid release rate under physiological conditions and contains 5-hydroxy tryptophan and said retard layer containing either tryptophan or 5-hydroxy tryptophan and having a retarded release rate under physiological conditions.

2. A tablet according to claim 1, in which the fast layer contains 5-hydroxytryptophan and the retard layer contains tryptophan.

3. A tablet according to claim 1, in which the fast layer contains 5-hydroxytryptophan and the retard layer contains 5-hydroxytryptophan.

4. A tablet according to claim 1, in which in which 5-hydroxytryptophan is of natural extractive origin.

5. A tablet according to claim 4, in which 5-hydroxytryptophan is in the form of an extract from *Griffonia simplicifolia*.

6. A tablet according to claim 1, where tryptophan is L-Tryptophan.

7. A tablet according to claim 1, in which the 5-hydroxytryptophan contents in the fast layer comprise between 1 and 40% of the weight of said layer.

8. A tablet according to claim 7, in which the 5-hydroxytryptophan contents comprise between 6 and 25% of the weight of said layer.

9. A tablet according to claim 1, in which the layer contains tryptophan, and the tryptophan contents comprises between 10 and 70% of the weight of said layer.

10. A tablet according to claim 9, in which the tryptophan content comprises between 20 and 40% of the weight of said layer.

11. A tablet according to claim 1, in which the retard layer contains 5-hydroxytryptophan where the 5-hydrohytryptophan content comprises between 10 and 70% of the weight of the layer.

12. A tablet according to claim 11, in which the 5-hydroxytryptophan content comprises between 20 and 40% of the weight of said layer.

13. A bi-layer tablet having a fast and a retarded layer said fast layer being a fast layer which possesses a rapid release rate under physiological conditions and contains 5-hydroxy tryptophan, and the retarded layer contains tryptophan and possesses a retarded release rate under physiological conditions.

14. A bilayer tablet having a fast and a retarded layer said fast layer being a fast layer which possesses a rapid release rate under physiological conditions and contains 5-hydroxytryptophan, and the retarded layer contains 5-hydroxytryptophan and possesses a retarded release rate under physiological conditions.

* * * * *

UNITED STATES PATENT AND TRADEMARK OFFICE
CERTIFICATE OF CORRECTION

| | | |
|---|---|---|
| PATENT NO. | : 7,670,619 B2 | Page 1 of 1 |
| APPLICATION NO. | : 11/201070 | |
| DATED | : March 2, 2010 | |
| INVENTOR(S) | : Bojidar Mihaylov Stankov | |

It is certified that error appears in the above-identified patent and that said Letters Patent is hereby corrected as shown below:

Title Page

(75) Inventor: Bojidar Mihaylov, Milan (IT)

should read:

(75) Inventor: Bojidar Mihaylov Stankov, Milan (IT)

Signed and Sealed this

Twenty-eighth Day of September, 2010

David J. Kappos
*Director of the United States Patent and Trademark Office*